US009182337B2

(12) United States Patent
Kamee et al.

(10) Patent No.: US 9,182,337 B2
(45) Date of Patent: Nov. 10, 2015

(54) OBSERVATION APPARATUS CAPABLE OF DETECTING DISTAL END POSITION OF INSERTION MODULE USING EXTERNAL LIGHT

(71) Applicant: OLYMPUS CORPORATION, Tokyo (JP)

(72) Inventors: Hiroyuki Kamee, Koganei (JP); Eiji Yamamoto, Musashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 35 days.

(21) Appl. No.: 14/047,330

(22) Filed: Oct. 7, 2013

(65) Prior Publication Data
US 2014/0036259 A1 Feb. 6, 2014

Related U.S. Application Data

(63) Continuation of application No. PCT/JP2012/059248, filed on Apr. 4, 2012.

(30) Foreign Application Priority Data

Apr. 8, 2011 (JP) .................................. 2011-086597

(51) Int. Cl.
*G01B 11/14* (2006.01)
*G01N 21/01* (2006.01)
(Continued)

(52) U.S. Cl.
CPC ............ *G01N 21/01* (2013.01); *A61B 1/00009* (2013.01); *A61B 1/0661* (2013.01); *A61B 5/065* (2013.01); *G02B 23/2461* (2013.01)

(58) Field of Classification Search
CPC ....................................................... G01B 11/14

USPC .......................................................... 356/614
See application file for complete search history.

(56) References Cited

U.S. PATENT DOCUMENTS 8,831,710 B2    9/2014  Kobayashi
2005/0234526 A1  10/2005  Gilhuly et al.
(Continued)

FOREIGN PATENT DOCUMENTS

JP          4-90285 A      3/1992
JP      2002-028125 A      1/2002
(Continued)

OTHER PUBLICATIONS

Extended Supplementary European Search Report dated Sep. 1, 2014 from related European Application No. 12 76 8528.7.
(Continued)

*Primary Examiner* — Roy M Punnoose
(74) *Attorney, Agent, or Firm* — Scully, Scott, Murphy & Presser, PC

(57) ABSTRACT

An insertion module inserted into inside of an observed object includes a light-source light emitting module, around its distal end, configured to emitted light from a light source and a detector, provided close to the distal end, configured to detect a light quantity of incident visible light. A controller controls the light source such that a null signal is transmitted from the light-source light emitting module, the null signal being characteristic for detection of the position of the distal end and obtained by making at least light of a predetermined wavelength region have an absence of visible light. The detector performs detecting operation in a period in which the null signal is transmitted. A determination module performs determination relating to the position of the distal end, based on detection information outputted by the detector.

23 Claims, 4 Drawing Sheets

(51) Int. Cl.
    *G02B 23/24*     (2006.01)
    *A61B 1/00*     (2006.01)
    *A61B 1/06*     (2006.01)
    *A61B 5/06*     (2006.01)

(56) References Cited

U.S. PATENT DOCUMENTS

| | | | |
|---|---|---|---|
| 2007/0225560 A1* | 9/2007 | Avni et al. | 600/118 |
| 2008/0262299 A1 | 10/2008 | Niida et al. | |
| 2011/0015528 A1* | 1/2011 | Kobayashi | 600/477 |

FOREIGN PATENT DOCUMENTS

| | | |
|---|---|---|
| JP | 2004-187986 A | 7/2004 |
| JP | 2004-275321 A | 10/2004 |
| JP | 2007-532208 A | 11/2007 |
| JP | 2008-264252 A | 11/2008 |
| JP | 4316118 B2 | 8/2009 |
| JP | 2010-082041 A | 4/2010 |
| JP | 2011-19706 A | 2/2011 |
| JP | 2011-212194 A | 10/2011 |
| WO | 2009/008088 A1 | 1/2009 |

OTHER PUBLICATIONS

International Search Report dated Jun. 19, 2012 issued in PCT/JP2012/059248.

Japanese Office Action dated Mar. 3, 2015 from related Japanese Application No. 2011-086597, together with an English language translation.

* cited by examiner

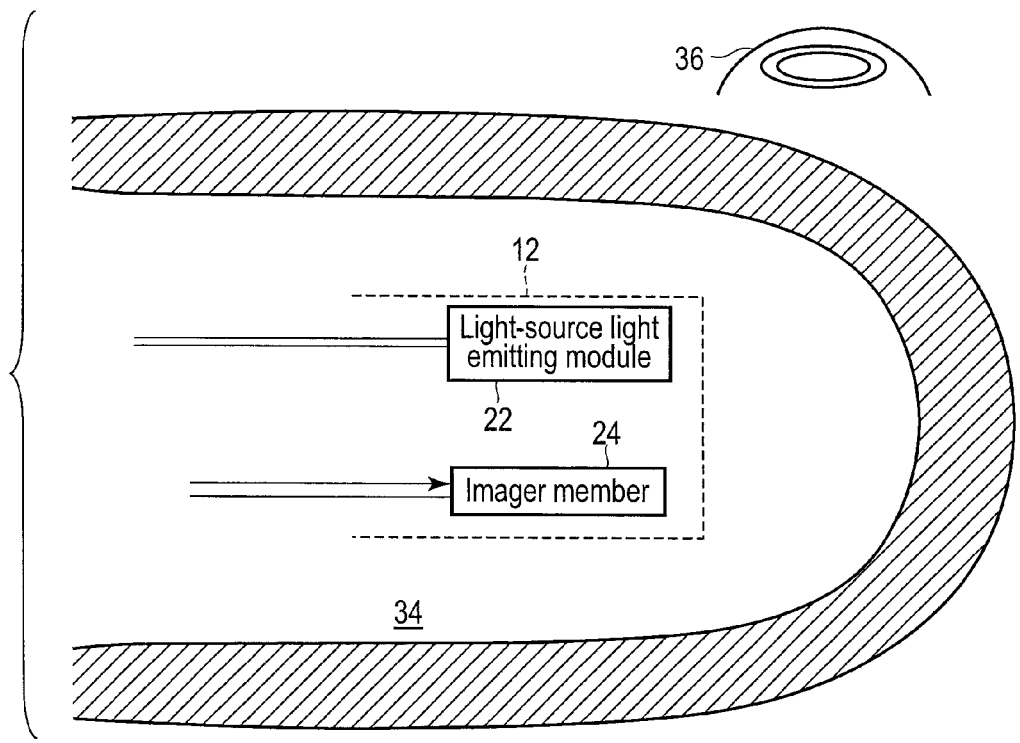
F I G. 6
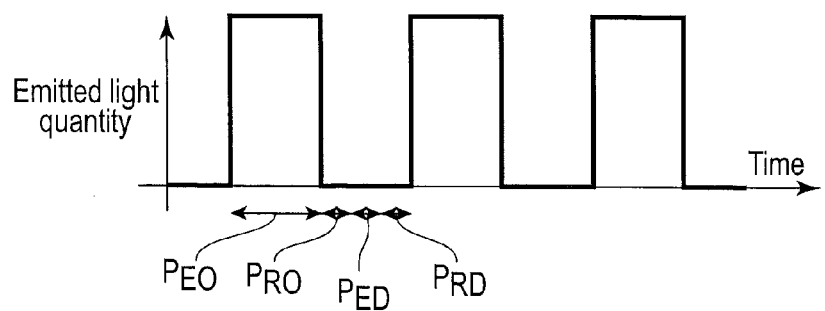
F I G. 7

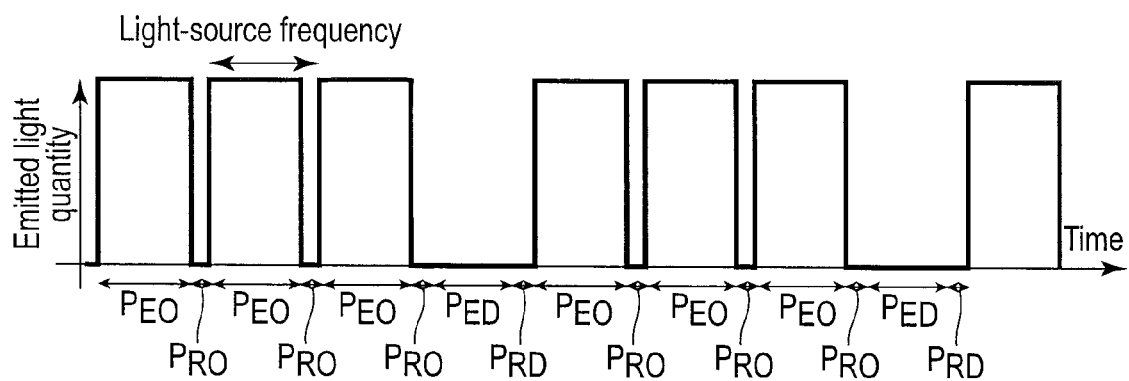
F I G. 8
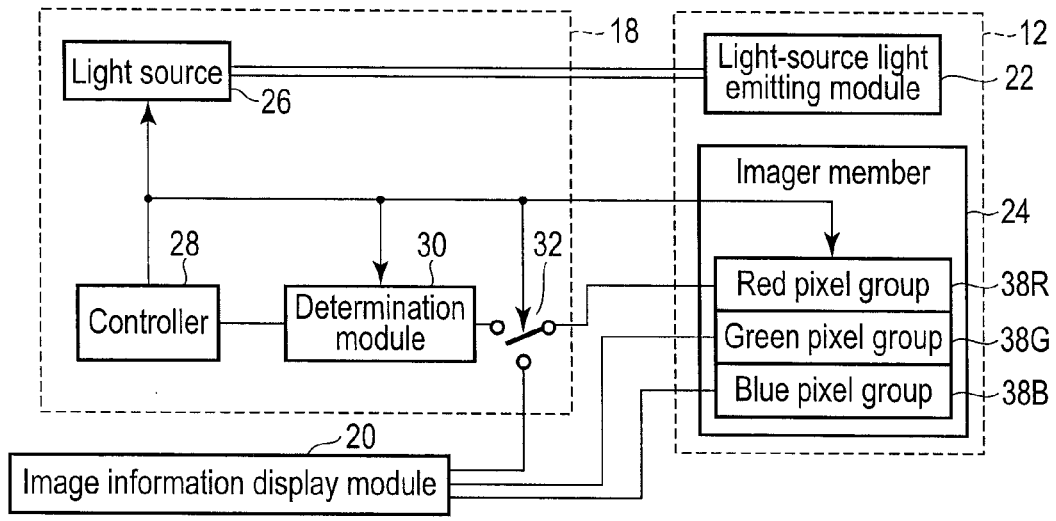
F I G. 9
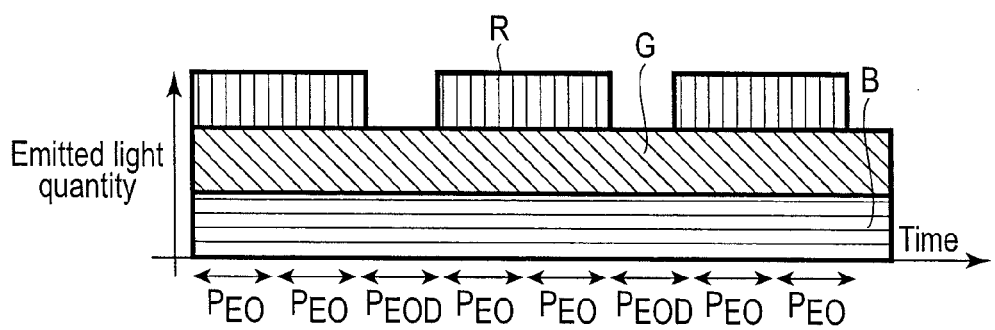
F I G. 10

OBSERVATION APPARATUS CAPABLE OF DETECTING DISTAL END POSITION OF INSERTION MODULE USING EXTERNAL LIGHT

CROSS-REFERENCE TO RELATED APPLICATIONS

This is a Continuation Application of PCT Application No. PCT/JP2012/059248, filed Apr. 4, 2012, which was published under PCT Article 21(2) in Japanese.

This application is based upon and claims the benefit of priority from prior Japanese Patent Application No. 2011-086597, filed Apr. 8, 2011, the entire contents of which are incorporated herein by reference.

BACKGROUND OF THE INVENTION

1. Field of the Invention

This invention relates to an observation apparatus which is capable of detecting a distal end position of an insertion module by using external light.

2. Description of the Related Art

Generally, considerably bright light sources are used in observation apparatuses to observe the inside or an internal wall of an observed object, such as endoscopes, to improve the observation accuracy. When the bright light quantity is maintained in the case where the member, which is inserted into the observed object to obtain observation information, is located outside the observed object, however, the observer or the test subject, who is a representative example of the observed object, may be dazzled, and the electrical energy is wasted. The visual function of the observer or the test subject may be damaged, according to the type of the light source and the light output amount. Thus, it is desired to properly control the light quantity of the light source, according to the position of the observation member for the observed object.

To meet the above demand, Japanese Patent No. 4316118 presents a technique of determining whether the insertion module is located inside the living body or outside the living body. The technique is detecting the position of the insertion module, by detecting an observed color by color detecting means attached to a distal end of the insertion module being a member used for observation, and comparing the observed color with a color signal obtained inside the living body serving as the observed object.

In Japanese Patent No. 4316118, the image observed with the distal end of the insertion module, in particular, color information thereof, is used as a determination standard for detecting the position of the insertion module. A reddish image similar to an image of the inside of the body may be obtained, however, even when the insertion module is located outside the body. In addition, color distribution is not uniform even in the body, and white or yellow regions may be observed. Thus, it is probable that the position (inside or outside of the body) of the observation module cannot be accurately detected, and the safety is not secured, or the observation is obstructed.

BRIEF SUMMARY OF THE INVENTION

The present invention has been made in view of the above points. The object of the present invention is to provide an observation apparatus, which is capable of securely detecting whether the distal end of the insertion module is located inside the observed object or outside the observed object, under any circumstances.

According to an aspect of the invention, there is provided an observation apparatus which observes inside of an observed object, comprising:

a light source configured to emit light;

an insertion module, which includes a light-source light emitting module around its distal end, configured to be inserted into inside of the observed object, the light-source light emitting module emitting light from the light source;

a detector, which is provided close to the distal end of the insertion module, configured to detect a light quantity of incident visible light;

a determination module configured to perform determination relating to a position of a distal end of the insertion module; and a controller configured to control the light source such that a null signal is transmitted from the light-source light emitting module, the null signal being characteristic for detection of the position of the distal end of the insertion module and obtained by making at least light of a predetermined wavelength region have an absence of visible light, wherein the detector performs detecting operation in a period in which the null signal is transmitted, and outputs detection information indicating a detection result, and the determination module performs the determination relating to the position of the distal end of the insertion module, based on the detection information outputted by the detector.

According to the present invention, an observation apparatus, which is capable of securely detecting whether the distal end of the insertion module is located inside the observed object or outside the observed object under any circumstances, is provided.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is a schematic diagram of a state where the distal end of the insertion module is located inside the observed objected, and a light source is off;

FIG. 7 is a schematic diagram illustrating operation of an imager member corresponding to change in light quantity;

FIG. 8 is a schematic diagram illustrating another example of the operation of the imager member corresponding to change in light quantity;

FIG. 9 is a schematic diagram illustrating connection relation between modules which form an observation apparatus according to a second embodiment of the present invention; and FIG. 10 is a schematic diagram illustrating operation of an imager member for output light from a light source.

DETAILED DESCRIPTION OF THE INVENTION

Embodiments of the present invention will now be explained with reference to drawings.

First Embodiment

Figure 1:
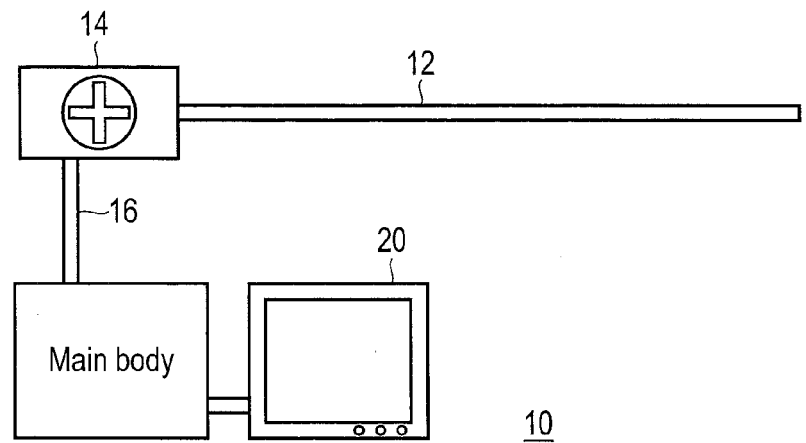
FIG. 1 is a schematic diagram illustrating a structure of an observation apparatus according to a first embodiment of the present invention.

As illustrated in FIG. 1, an observation apparatus 10 according to a first embodiment of the present invention includes an insertion module 12, an operating module 14, a connection cable 16, a main body 18, and an image information display module 20.

Figure 2:
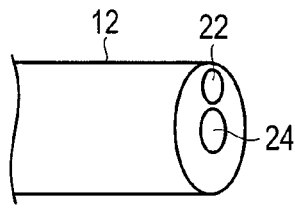
FIG. 2 is an enlarged view of a distal end part of an insertion module.

The insertion module 12 is a member which is inserted into an observed object, and can be curved in accordance with operation of the operating module 14 by the observer. As illustrated in FIG. 2, for example, a front surface of a distal end of the insertion module 12 is provided with a light-source light emitting module 22, which emits illumination light for observation, and an imager member 24, which is an observation image acquisition module to obtain visual information relating to the inside of the observed object. Examples of the imager member 24 are a charge-coupled device (CCD) image sensor, and a complementary metal oxide semiconductor (CMOS) image sensor. The visual information obtained by the imager member 24 is transmitted to the main body 18 through the insertion module 12, the operating module 14, and the connection cable 16, and displayed on the image information display module 20 connected to the main body 18.

Figure 3:
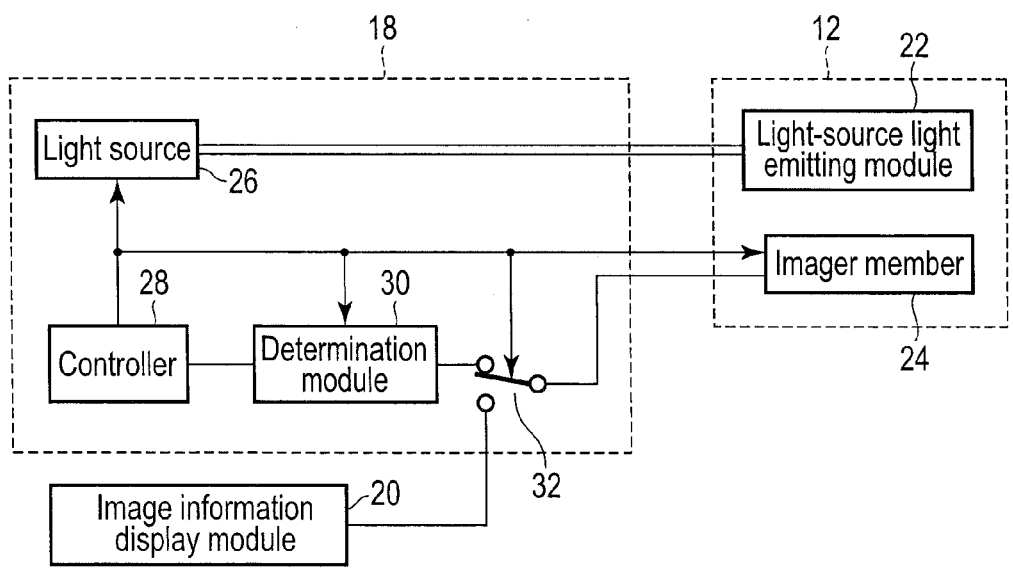
FIG. 3 is a schematic diagram illustrating a structure of a main body and connection relation between modules.

As illustrated in FIG. 3, the main body 18 is formed of a light source 26, a controller 28, a determination module 30, and a switch 32.

Representative examples of the light source 26 are a lamp, an LED, and a laser. Light-source light from the light source 26 is guided through the connection cable 16, the operating module 14, and the insertion module 12 to the distal end of the insertion module 12, by a light-guide member such as an optical fiber. The light-source light is emitted from the light-source light emitting module 22 to the front of the insertion module 12, as illumination light for observation. Specifically, the light source 26 serves as an observation light source which illuminates the inside of the observed object to observe the inside of the observed object by the imager member 24.

In addition, the imager member 24 is connected to an input terminal of the switch 32, which switches one input between two outputs, through the insertion module 12, the operating module 14, and the connection cable 16. One output terminal of the switch 32 is connected with the image information display module 20, and the other output terminal of the switch 32 is connected with the determination module 30. Thereby, the imager member 24 also functions as a detector, which detects a light quantity of the incident visible light. Specifically, the imager member 24 serves as both an observation image acquisition module and a detector.

The determination module 30 determines the position of the distal end of the insertion module 12. The determination module 30 is connected to the controller 28, to input a determination result thereof to the controller 28. The controller 28 is connected with the light source 26, the imager member 24, the determination module 30, and the switch 32, to control them. Details of control performed by the controller 28 will be described later.

Figure 4:
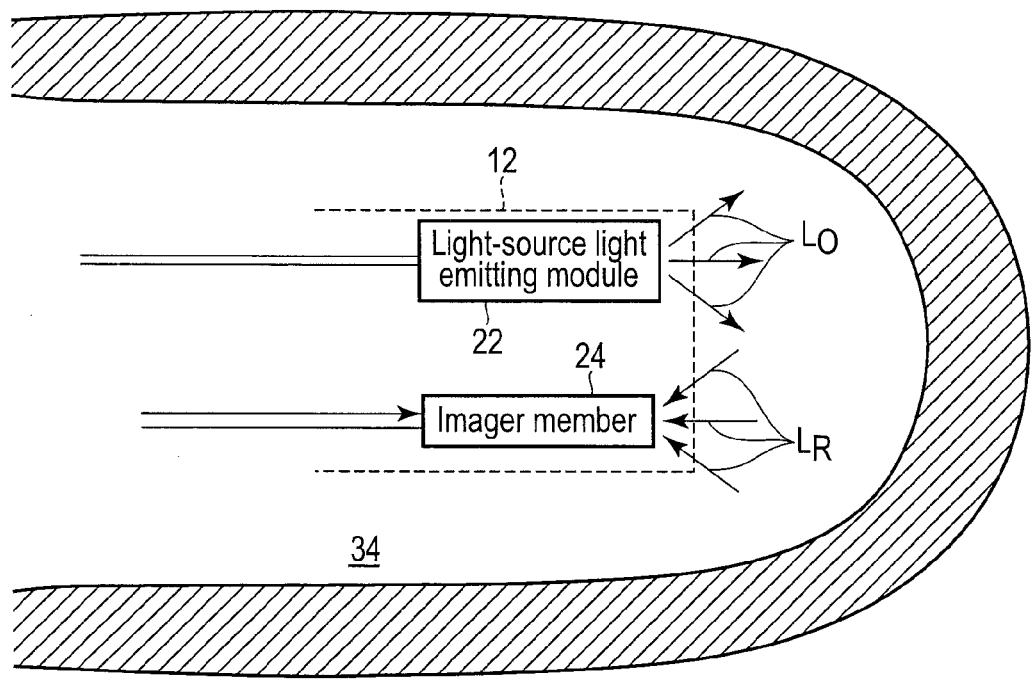
FIG. 4 is a schematic diagram of a state where the distal end of the insertion module is located inside an observed object.

First, as the whole system, white light serving as observation illumination light $L_O$ is emitted from the light-source light emitting module 22 provided on the distal end of the elongate insertion module 12, as illustrated in FIG. 4. Then, the imager member 24, which acquires an image of reflected light $L_R$ from the observed object, obtains image information which indicates the state of a part located in front of the distal end of the insertion module 12. The image information is displayed on the image information display module 20, and thereby the observer can observe an internal observed object 34.

As a work process, first, the image information display module 20 and the light source 26 are driven by the observer's operation. Next, the insertion module 12 is inserted into an inlet of the observed object, which connects to the internal observed object 34. In this state, the observer operates the operating module 14 and pulls and pushes the insertion module 12 itself. Thereby, the observer controls the position and the direction of the distal end of the insertion module 12, moves the distal end of the insertion module 12 to a region of the internal observed object 34 to be observed, and performs observation. When the observation is finished, the observer pulls out the insertion module 12, while the light source 26 is kept turned on and the imager member 24 is kept driven, to prevent the insertion module 12 from damaging the internal observed object 34. After the observer verifies that the distal end of the insertion module 14 has been taken out of the observed object, the light source 26 is turned off by observer's operation, and drive of the imager member 24 is ended.

Figure 5:
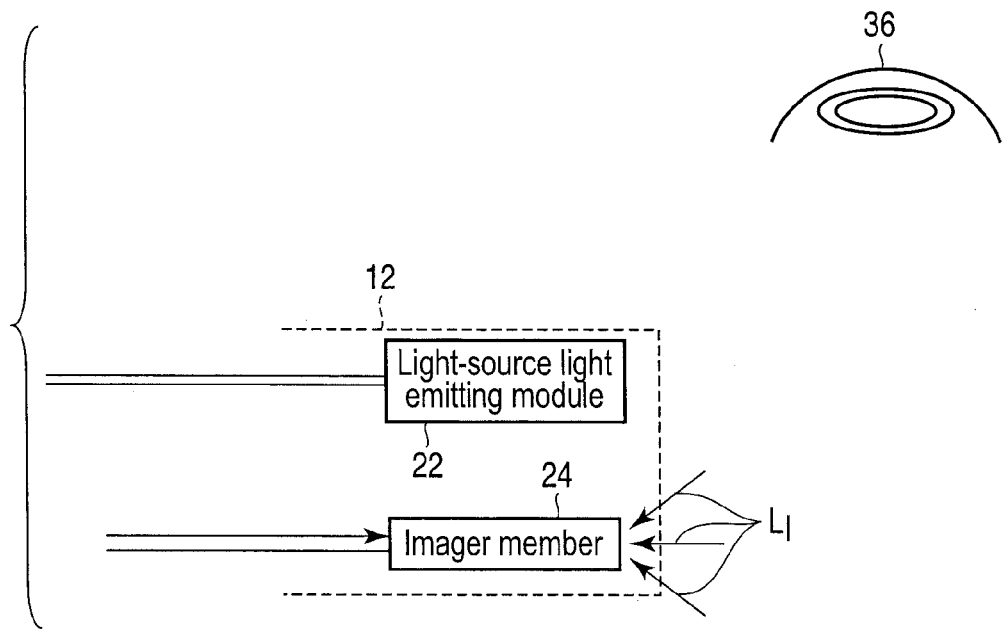
FIG. 5 is a schematic diagram of a state where the distal end of the insertion module is located outside the observed objected, and a light source is off.

Generally, an indoor lighting is attached to the room where observation is performed, to perform the observation work smoothly. Thus, as illustrated in FIG. 5, when the distal end of the insertion module 12 is located outside the observed object, the imager member 24 receives indoor illumination light $L_I$ from the indoor lighting 36, and obtains a sufficient light quantity, even when the light source 26 is off. On the other hand, as illustrated in FIG. 6, when the distal end of the insertion module 12 is located in the internal observed object 34 and the light source 26 is off, the imager member 24 can receive light of considerably minute light quantity. Specifically, in such a case, the received light has considerably minute light quantity, since it is limited to indoor illumination light $L_I$ from the indoor lighting 36, which has transmitted through the observed object from the outside to the inside, and light stored in the internal observed object 34 with the observation illumination light $L_O$ emitted from the light-source light emitting module 22 when the light source 26 was on. Thus, it is possible to accurately determine whether the distal end of the insertion module 12 is located inside the observed object or outside the observed object, by turning on and off the light source 26, performing image acquisition operation by the imager member 24 in timing that the light source 26 is off, and determining the light quantity of the received light.

Thus, in the present embodiment, the light source 26 is not kept turned on, but first turned on and off repeatedly, when the light source 26 is turned on in response to the observer's operation of turning on the system power supply. The controller 28 controls the light quantity and the timing of repeatedly turning on and off the light source 26 in this operation. Then, the controller 28 controls the light quantity based on a determination result obtained by the determination module 30. The light quantity control performed in this operation is not light quantity control performed to obtain proper information when the object is observed. The light quantity control performed in this operation is performed to secure the safety for the observer and others when the distal end of the insertion module 12 is located outside the observed object, to remove the observer's discomfort caused by the dazzling light, or to avoid wasteful consumption of electrical energy. Thus, the control system is different from the control system used for controlling the light quantity when the object is observed.

The present embodiment shows an example of controlling light quantity for the purpose of securing safety for the observer and others.

There are two types of determination results obtained by the determination module 30. One is a determination result that "the distal end of the insertion module 12 is located outside the observed object". The other is a determination result that "the distal end of the insertion module 12 is located inside the observed object". When the determination module 30 obtains a determination result that "the distal end of the insertion module 12 is located outside the observed object", the controller 28 receives the result, and adjusts the light source 26 to adjust the light quantity to a safe light quantity which does not have any harmful influence on human eyes. In addition, when the determination module 30 obtains a determination result that "the distal end of the insertion module 12 is located inside the observed object", the controller 28 adjusts the light source 26 to adjust the light quantity to an observation light quantity suitable for observation. The safe light quantity is considerably smaller than the observation light quantity. The determination module 30 generates the above two types of determination results, based on the image information obtained by the imager member 24 located at the distal end of the insertion module 12. Next, specific operation for the above will be explained hereinafter.

The imager member 24 includes a plurality of light quantity receiving elements (pixels) arranged in rows and columns. The imager member 24 performs image acquisition operation once in a period in which the light source 26 is on, and once in a period in which the light source 26 is off, as illustrated in FIG. 7. In FIG. 7, the period in which the light source 26 is on is a period in which the emitted light quantity LE is at high level. In the following explanation, image acquisition operation performed in a period in which the light source 26 is on is referred to as "observation image acquisition operation", and image acquisition operation performed in a period in which the light source 26 is off is referred to as "position-detection image acquisition operation". One of imager members used at present requires an exposure period, in which the incident light quantity is received and the received light quantity is converted into an electrical signal corresponding to the received light quantity, and a data reading period in which the information is transmitted. The meaning of the term "image acquisition operation" in this explanation is limited to "exposure operation". Specifically, the period in which "observation image acquisition operation" is performed is "observation exposure period $P_{EO}$" in FIG. 7, and the period in which position-detection image acquisition operation is performed is "insertion-module distal-end-position determination exposure period $P_{ED}$" in FIG. 7. The respective information items obtained in the above two exposure periods are transmitted to the main body 18, in "observation data reading period $P_{RO}$" or "insertion-module distal-end-position determination data reading period $P_{RD}$".

The present embodiment shows an example in which all the light is turned off, as a characteristic null signal for detecting the distal end position of the insertion module 12, which is transmitted from the light-source light emitting module 22. Specifically, a null signal is a signal which there is an absence of light of at least a specific wavelength region in the intensity of light from the light source 26, or in the visible light. In the present embodiment, the null signal is a signal in which there is an absence of light of all the wavelength regions of visible light.

The controller 28 controls the light source 26 such that such a null signal is transmitted from the light-source light emitting module 22, and performs control to cause the imager member 24 functioning as the detector to perform image acquisition operation in a period in which the null signal is transmitted. The controller 28 also controls the switch 32 and the determination module 30, to switch the switch 32 to the determination module 30 side and cause the determination module 30 to perform determination. Specifically, in the "insertion-module distal-end-position determination exposure period $P_{ED}$" and the "insertion-module distal-end-position determination data reading period $P_{RD}$", the switch 32 is switched to the determination module 30 side. Thereby, the detection information obtained by the position-detection image acquisition operation and transmitted from the imager member 24 functioning as the detector is transmitted to the determination module 30 as the position-detection image information. In the "observation exposure period $P_{EO}$" and "observation data reading period $P_{RO}$", the switch 32 is switched to the image information display module 20 side. Thereby, the observation image information from the imager member 24 is transmitted to the image information display module 20, and presented to the observer as the observation image.

The determination module 30 uses the maximum light quantity, as a determination index, among the image information items included in the position-detection image information. When the determination index is equal to or greater than a threshold light quantity, the determination module 30 generates a determination result that "the distal end of the insertion module 12 is located outside the observed object". Conversely, when the determination index is less than the threshold light quantity, the determination module 30 generates a determination result that "the distal end of the insertion module 12 is located in the observed object inside 34".

In this processing, when the determination module 30 generates an erroneous determination result, observation may not be normally performed, or the safety of eyes of the observer and others may be damaged. Thus, erroneous determination should be prevented. A first situation which causes erroneous determination is a situation in which an object of low reflectance is located in front of the distal end of the insertion module 12, although the distal end of the insertion module 12 is located outside the observed object. In view of this, the imager member 24 desirably includes an imager element or an optical system which can acquire an image of a range of a wide angle. To prevent the determination module 30 from erroneously determining that the distal end is located inside the observed object in the above situation, it is necessary to determine the distal end position of the insertion module 12 more accurately, by acquiring an image of a range of a wide angle in front of the distal end of the insertion module 12 and receiving the surrounding light as much as possible.

Also in this processing, the determination module 30 generates a determination result, by picking up the maximum light quantity among the position-detection image information items as the determination index, and providing the numerical value thereof with a certain threshold light quantity. This is because the distal end position of the insertion module 12 should be located outside the observed object, when light quantity equal to the indoor illumination light is received from a direction, even when the imager member 24 detects low light quantity from the whole part located in front of the distal end of the insertion module 12.

A second situation which causes erroneous determination of the determination module 30 is a situation in which the observer or another person covers the distal end of the insertion module 12 by the hand. Also in this case, however, the determination module 30 can determine that the distal end of the insertion module is located outside the observed object, as long as the imager member 24 receives even a small light quantity equal to the indoor illumination light through a space between the observer's fingers. When the distal end of the insertion module 12 is covered without any space, the light-source light emitting module 22 is entirely covered, and thus the safety for human eyes is secured, even when the determination module 30 erroneously determines that the distal end of the insertion module 12 is located in the internal observed object 34 and light of the observation light quantity is emitted.

Although the light source 26 is placed in the main body 18 in the present embodiment, the structure is not limited to it. A small light source 26 such as an LED may be placed in the distal end of the insertion module 12.

In addition, although the present embodiment shows the example in which the light source 26 is turned on and off repeatedly and observation image acquisition operation and position-detection image acquisition operation are periodically repeated, the structure is not limited to it. Determination is accurately performed, also in the case where observation image acquisition operation is performed with the light source 26 turned on, and position-detection image acquisition operation is performed with the light source 26 turned off only when it is necessary to detect the position of the distal end of the insertion module 12. In addition, as illustrated in FIG. 8, accurate determination is performed also in the case where position-detection image acquisition operation is performed once each time when observation image acquisition operation is performed several times.

Although the maximum light quantity among the detection information items is used as the determination index for the determination module 30 in the present embodiment, the structure is not limited to it. Since the imager member 24 may perform erroneous detection only from a numerical value of a pixel, that is, light quantity of a pixel, the determination module 30 may perform determination based on a plurality of detection information items in a descending order from the maximum light quantity, among the detection information items.

Besides, although the present embodiment shows the example in which the imager member 24 placed in the distal end of the insertion module 12, the structure is not limited to it. Specifically, a lens or a distal end of a fiber may be arranged in the distal end of the insertion module 12, the received optical information may be guided by the fiber or the relay lens, and the image information may be obtained by, for example, a CCD image sensor attached to the inside of the operating module 14 located at the other end of the insertion module 12. It is also possible to guide the received light by the fiber through the operating module 14 and the connection cable 16, and obtain the image information by, for example, a CCD image sensor attached to the inside of the main body 18.

Although the present embodiment shows a detector which also serves as the observation image acquisition module, the structure is not limited to it. A plurality of detectors may be provided in the vicinity of the distal end of the insertion module 12 along the insertion direction, to enhance the accuracy of detection of the distal end position of the insertion module 12. In this structure, it is more desirable to determine that the distal end of the insertion module 12 is located in the internal observed object 34, when the maximum value in determination indexes obtained by the detectors, or the maximum value in the determination indexes from the detectors which are continuously provided from the distal end is less than a threshold light quantity.

Although the determination index for the determination module 30 is obtained from one detection information item in the present embodiment, the structure is not limited to it. Since the imager member 24 may perform erroneous detection only from one detection information item, it is desirable to perform determination based on a plurality of detection information items which are successive in time.

Although the present embodiment shows the example in which the imager member 24 detects only the light quantity and cannot detect color information of the observed object, the structure is not limited to it. The present embodiment is applicable to a color observation apparatus in which the imager member 24 includes pixels of three primary colors, that is, a red pixel group which detects a red wavelength component light quantity, a green pixel group which detects a green wavelength component light quantity, and a blue pixel group which detects a blue wavelength component light quantity. Specifically, the position of the distal end of the insertion module 12 can be detected, by providing the position-detection image information item of the three-primary-color pixel groups with respective threshold light quantities to use them as the determination standards, or providing position-detection image information of one primary color among the three-primary-color pixel groups with a threshold light quantity to use it as the determination standard.

Although the present embodiment shows the example in which light of one type is emitted from the light source 26 and turned on and off repeatedly, the structure is not limited to it. The present embodiment is also applicable to a color observation apparatus in which light source 26 which successively emits red light, green light, and blue light in a time-division manner is used in combination with imager member 24 which is capable of receiving a light quantity of visible light. Specifically, the light source 26 is successively turned on in the order of red, green, blue, red, green, blue, . . . , for example, a period in which light of all the colors is turned off is provided directly after each period in which blue light is turned on, and thereby the position of the distal end of the insertion module 12 can be detected from the image information obtained in the above period.

When a region to be observed by the observer is located inside a part close to the boundary between the inside and the outside of the observed object, it is desirable that an external light shield member, which shuts off external light, such as light from the indoor lighting 36, is provided in the vicinity of the boundary. The external light shield member is formed of material having a characteristic of shutting off (absorbing, reflecting, or scattering) visible light, and has an external diameter approximately equal to the inlet diameter located close to the boundary between the inside and the outside of the observed object. The external light shield member includes a through hole in it, and the diameter of the through hole is approximately equal to or slightly greater than the diameter of the insertion module 12. By using the external light shield member having the above structure and formed of the above material, no external light enters the internal observed object 34 located close to the boundary, and accurate observation can be performed even in the region close to the boundary. For example, in the case of using an endoscope configured to observe person's internal organs through the human's mouth, a member which is called a mouthpiece and fits the size of the human's mouth is used to improve the operability. The function of the above external light shield member may be added to the mouthpiece.

As described above, according to the present embodiment, detection operation to detect the position of the insertion module 12 is performed in a period in which the light source 26 is off. Thus, it is possible to determine whether the distal end of the insertion module 12 is located outside the observed object under the indoor illumination light, or located in the internal observed object 34 which no general illumination light reaches. Specifically, it is possible to securely detect whether the distal end of the insertion module 12 is located inside or outside the observed object, under any circumstances.

In addition, since detection for detecting the position of the insertion module 12 is performed by using the imager member 24 being the observation image acquisition module used for the original purpose, the number of the members does not much increase, the apparatus requires small cost, and the volume of the apparatus increases little.

Besides, since the light source 26 is turned off at the timing to prevent erroneous detection of the determination module, the position of the distal end of the insertion module 12 can be accurately determined. Specifically, since the light source 26 is off during a period in which the determination module is performing detecting operation, the determination module can accurately perform detecting operation.

In the present embodiment, since all the visible lights which can be emitted by the light source 26 are turned off, the technique is applicable to observation apparatuses including an any type of imager member which can detect visible light.

In addition, the imager member 24 being the observation imager member is used as the detector in the present embodiment, and detection can be performed with a plurality of pixels. Besides, since the maximum light quantity is used as the determination index among the image information items, the position of the distal end of the insertion module 12 can be accurately detected, based on a plurality of information items with a certain angle range.

In the present embodiment, since one threshold light quantity is used as the determination standard, the determination module 30 has a simple structure, and the manufacturing cost is reduced.

In the present embodiment, since the position of the distal end of the insertion module 12 is periodically determined, the safety and the observation accuracy are continuously maintained.

In the present embodiment, since determination is performed based on a plurality of detection information items which are successive in time, erroneous determination is prevented, and the position of the distal end of the insertion module 12 can be accurately detected.

In the present embodiment, since the external light shield member is placed in the vicinity of the boundary between the inside and the outside of the observed object, the region close to the inlet of the observed object is not brightly illuminated with external light such as the indoor lighting, and the internal observed object 34 close to the inlet can be accurately observed.

Second Embodiment

Next, an observation apparatus 10 according to a second embodiment of the present invention will be explained hereinafter. In the present embodiment, only constituent elements which are different from those of the first embodiment will be explained, and explanation of common constituent elements will be omitted. The structure of the observation apparatus 10 according to the second embodiment is different from that of the first embodiment in the following points.

Specifically, as illustrated in FIG. 9, an imager member 24 includes three-primary-color pixel groups. The groups include a red pixel group 38R which detect a light quantity of the incident red wavelength component, a green pixel group 38G which detects a light quantity of the green wavelength component, and a blue pixel group 38B which detects a light quantity of the blue wavelength component. In the imager member 24 having the above structure, the color pixel groups are connected to different components. In the present embodiment, the green pixel group 38G and the blue pixel group 38B are connected to an image information display module 20, and the red pixel group 38R is connected to a switch 32. One output terminal of the switch 32 is connected with the image information display module 20, and the other output terminal of the switch 32 is connected with a determination module 30.

A light source 26 is configured to be capable of transmitting a null signal, in which there is an absence of one of the three primary colors, for example, a red component. As illustrated in FIG. 10, a controller 28 controls the light source 26 to cause the light source 26 to alternately emit white light, which includes a red component R, a green component G, and a blue component B, as the observation illumination light, and blue-green light, in which there is an absence of a red component R in the white light, as a position-detection null signal. The controller 28 also performs control to cause the red pixel group 28R functioning as a detector to perform image acquisition operation in a period in which a null signal is transmitted. The controller 28 also switches the switch 32 to the determination module 30 side, to cause the determination 30 to perform determination.

As operation, the second embodiment is different from the first embodiment in the following points. Specifically, in a period in which the observation illumination light is on (observation exposure period $P_{EO}$), all the three-primary-color pixel groups of the imager member 24 operate as the observation image acquisition module. In comparison with this, in a period in which a null signal is transmitted (detection and observation exposure period $P_{EOD}$), the green pixel group 38G and the blue pixel group 38B of the imager member 24 continue to operate as the observation image acquisition module, and the red pixel group 38R operates as a detector for detecting the distal end position of the insertion module 12.

Thus, in the present embodiment, the red pixel group 38R is a observation and position-detection pixel group, and the green pixel group 38G and the blue pixel group 38B are observation pixel groups. So, in FIG. 9, the imager member 24 is connected with the image information display module 20 and the determination module 30. Specifically, the red pixel group 38R is selectively connected to the image information display module 20 and the determination module 30 through the switch 32, while the green pixel group 38G and the blue pixel group 38B of the imager member 24 are connected only to the image information display module 20.

The determination module 30 determines that "the distal end of the insertion module 12 is located outside the observed object", when the maximum light quantity among the transmitted detection red information group is equal to or greater than a threshold light quantity. Conversely, the determination module 30 determines that "the distal end of the insertion module 12 is located inside the internal observed object 34", when the maximum light quantity is less than the threshold light quantity.

The following are assumed situations during observation.

In many cases, an indoor lighting 36 is attached to the room where observation is performed. Thus, when the distal end of the insertion module 12 is located outside the observed object, the red pixel group 38 of the imager member 24 can receive part of the illumination light, and transmit information items of a sufficient light quantity to the determination module 30, even when the light from the light source 26 does not include red wavelengths.

On the other hand, when the distal end of the insertion module 12 is located in the observed object inside 34, the light received by the red pixel group 38R of the imager member 24 has a considerably minute light quantity, such as a red wavelength being a part of the illumination light which has transmitted through the external surface of the observed object, and a red component of fluorescence of the internal surface of the observed object, which is obtained by the blue-green light of the light-source light.

To deal with the difference in situation between them, a threshold light quantity is set for the maximum light quantity among the red information items received by the red pixel group 38R. In addition, unlike the first embodiment, only the red wavelength is used when the position of the insertion module 12 is detected, and thus light of the other wavelengths and the primary-color pixel groups 48G and 38B can continue the observation operation.

Although the red wavelength is used for detecting the position of the distal end of the insertion module 12 in the present embodiment, the structure is not limited to it. Any color may be used as long as it is a primary color which colors the observation image, or a plurality of primary colors may be simultaneously used as determination indexes. In addition, the same color is not always used for detecting the position of the insertion module 12. In such a case, the primary-color pixel group connected to the image information display device and the determination module 30 differs according to the situation, and thus it is necessary to provide each primary-color pixel group with a switch.

In the present embodiment, since the imager member 24 located at the distal end of the insertion module 12 can be used as a detector, it is unnecessary to attach any special device to the distal end of the insertion module 12, and it can be easily detected whether the distal end of the insertion module 12 is located inside or outside the observed object.

In addition, since image information of colors other than the target color is continuously received even in the operation of detecting the distal end position of the insertion module 12, a loss in the image is small.

Although the present invention has been explained above based on the embodiments, the present invention is not limited to the above embodiments, but various modifications or applications can be performed within a range of the gist of the present invention, as a matter of course.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An observation apparatus for observing an inside of an observed object, the observation apparatus comprising:
   an elongated insertable structure configured to be removably inserted into the inside of the observed object;
   a light source configured to be controlled to:
      in an observation image acquisition operation, emit an observation light in an observation wavelength region; and
      in a detection image acquisition operation, emit one of no light and a detection light in a detection wavelength region different from the observation wavelength region,
      wherein the light source is operatively positioned relative to the elongated insertable structure to emit the observation light and the detection light from the elongated insertable structure;
   an image sensor configured to be controlled to:
      in the observation image acquisition operation, acquire an observation image; and
      in the detection image acquisition operation, acquire a detection image;
   a controller configured to switch between:
      the observation image acquisition operation where the controller controls the light source to emit the observation light in the observation wavelength region, and controls the image sensor to acquire the observation image; and
      the detection image acquisition operation where the controller controls the light source to emit the one of no light and the detection light in the detection wavelength region different from the observation wavelength region, and controls the image sensor to acquire the detection image; and
   a processor comprising hardware, wherein the processor is configured to implement a determination module configured to determine whether the elongated insertable structure is inserted into the inside of the observed object based on the detection image acquired in the detection image acquisition operation,
   wherein the controller is further configured to control the light source to emit a controlled light in response to a determination by the processor that the elongated insertable structure is not inserted into the inside of the observed object, wherein a light quantity of the controlled light is smaller than a light quantity of the observation light.

2. The observation apparatus according to claim 1, wherein the observation wavelength region is a wavelength region of visible light, and
   wherein in the detection image acquisition operation, the controller is configured to control the light source to emit no light.

3. The observation apparatus according to claim 2, wherein the image sensor comprises a plurality of pixels, wherein each of the plurality of pixels is configured to detect a light quantity of light in the detection wavelength region, and
   wherein the determination module is configured to determine whether the elongated insertable structure is inserted into the inside of the observed object based on one of:
      a maximum light quantity of the plurality of light quantities detected by the plurality of pixels of the image sensor; and
      the plurality of light quantities in a descending order from the maximum light quantity,
   wherein the one of the maximum light quantity and the plurality of light quantities in the descending order is a determination index.

4. The observation apparatus according to claim 3, wherein the determination module is configured to determine that the elongated insertable structure is not inserted into the inside of the observed object based on a determination that the determination index is equal to or greater than a threshold light quantity, and wherein the determination module is configured to determine that the elongated insertable structure is inserted into the inside of the observed object based on a determination that the determination index is less than the threshold light quantity.

5. The observation apparatus according to claim 4, wherein the controller is configured to perform the detection image acquisition operation a plurality of times to acquire a plurality of the detection image, and wherein the determination module is configured to determine that the elongated insertable structure is inserted into the inside the observed object based on a determination that the determination index associated with the plurality of the detection image is successively less than the threshold light quantity a plurality of times in time.

6. The observation apparatus according to claim 1, wherein the image sensor comprises a plurality of pixels, wherein each of the plurality of pixels is configured to detect a light quantity of light in the detection wavelength region, and wherein the determination module is configured to determine whether the elongated insertable structure is inserted into the inside of the observed object based on one of:
   a maximum light quantity of the plurality of light quantities detected by the plurality of pixels of the image sensor; and
   the plurality of light quantities in a descending order from the maximum light quantity,
   wherein the one of the maximum light quantity and the plurality of light quantities in the descending order is a determination index.

7. The observation apparatus according to claim 6, wherein the determination module is configured to determine that the elongated insertable structure is not inserted into the inside of the observed object based on a determination that the determination index is equal to or greater than a threshold light quantity, and wherein the determination module is configured to determine that the elongated insertable structure is inserted into the inside of the observed object based on a determination that the determination index is less than the threshold light quantity.

8. The observation apparatus according to claim 7, wherein the controller is configured to perform the detection image acquisition operation a plurality of times to acquire a plurality of the detection image, and wherein the determination module is configured to determine that the elongated insertable structure is inserted into the inside the observed object based on a determination that the determination index associated with the plurality of the detection image is successively less than the threshold light quantity a plurality of times in time.

9. The observation apparatus according to claim 1, wherein the observation light is white light.

10. An observation apparatus for observing an inside of an observed object, the observation apparatus comprising:
   an elongated insertable structure configured to be removably inserted into the inside of the observed object;
   a light source configured to be controlled to:
      in an observation image acquisition operation, emit an observation light in an observation wavelength region; and
      in a detection image acquisition operation, emit a detection light in a detection wavelength region different from the observation wavelength region,
      wherein the light source is operatively positioned relative to the elongated insertable structure to emit the observation light and the detection light from the elongated insertable structure;
   an image sensor configured to be controlled to:
      in the observation image acquisition operation, acquire an observation image; and
      in the detection image acquisition operation, acquire a detection image;
   a controller configured to switch between:
      the observation image acquisition operation where the controller controls the light source to emit the observation light in the observation wavelength region, and controls the image sensor to acquire the observation image; and
      the detection image acquisition operation where the controller controls the light source to emit the detection light in the detection wavelength region different from the observation wavelength region, and controls the image sensor to acquire the detection image; and
   a processor comprising hardware, wherein the processor is configured to implement a determination module configured to determine whether the elongated insertable structure is inserted into the inside of the observed object based on the detection image acquired in the detection image acquisition operation.

11. The observation apparatus according to claim 10, wherein the observation wavelength region is a wavelength region of visible light, and wherein in the detection image acquisition operation, the controller is configured to control the light source to emit no light.

12. The observation apparatus according to claim 11, wherein the image sensor comprises a plurality of pixels, wherein each of the plurality of pixels is configured to detect a light quantity of light in the detection wavelength region, and wherein the determination module is configured to determine whether the elongated insertable structure is inserted into the inside of the observed object based on one of:
   a maximum light quantity of the plurality of light quantities detected by the plurality of pixels of the image sensor; and
   the plurality of light quantities in a descending order from the maximum light quantity,
   wherein the one of the maximum light quantity and the plurality of light quantities in the descending order is a determination index.

13. The observation apparatus according to claim 12, wherein the determination module is configured to determine that the elongated insertable structure is not inserted into the inside of the observed object based on a determination that the determination index is equal to or greater than a threshold light quantity, and wherein the determination module is configured to determine that the elongated insertable structure is inserted into the inside of the observed object based on a determination that the determination index is less than the threshold light quantity.

14. The observation apparatus according to claim 13, wherein the controller is configured to perform the detection image acquisition operation a plurality of times to acquire a plurality of the detection image, and wherein the determination module is configured to determine that the elongated insertable structure is inserted into the inside the observed object based on a determination that the determination index associated with the plurality of the detection image is successively less than the threshold light quantity a plurality of times in time.

15. The observation apparatus according to claim 10,
wherein the image sensor comprises a plurality of pixels,
  wherein each of the plurality of pixels is configured to detect a light quantity of light in the detection wavelength region, and
  wherein the determination module is configured to determine whether the elongated insertable structure is inserted into the inside of the observed object based on one of:
    a maximum light quantity of the plurality of light quantities detected by the plurality of pixels of the image sensor; and
    the plurality of light quantities in a descending order from the maximum light quantity,
    wherein the one of the maximum light quantity and the plurality of light quantities in the descending order is a determination index.

16. The observation apparatus according to claim 15,
wherein the determination module is configured to determine that the elongated insertable structure is not inserted into the inside of the observed object based on a determination that the determination index is equal to or greater than a threshold light quantity, and
wherein the determination module is configured to determine that the elongated insertable structure is inserted into the inside of the observed object based on a determination that the determination index is less than the threshold light quantity.

17. The observation apparatus according to claim 16,
wherein the controller is configured to perform the detection image acquisition operation a plurality of times to acquire a plurality of the detection image, and
wherein the determination module is configured to determine that the elongated insertable structure is inserted into the inside the observed object based on a determination that the determination index associated with the plurality of the detection image is successively less than the threshold light quantity a plurality of times in time.

18. The observation apparatus according to claim 10, wherein the observation light is white light.

19. The observation apparatus according to claim 10, further comprising:
  a display configured to display the observation image,
  wherein the image sensor comprises:
    a first pixel corresponding to a red wavelength; and
    a second pixel corresponding to a green wavelength or a blue wavelength;
  wherein the first pixel is selectively connected to one of the display and the processor, and
  wherein the second pixel is only connected to the display.

20. An observation apparatus for observing an inside of an observed object, the observation apparatus comprising:
  an elongated insertable structure configured to be removably inserted into the inside of the observed object;
  a light source configured to be controlled to:
    in an observation image acquisition operation, emit an observation light in an observation wavelength region; and
    in a detection image acquisition operation, emit one of no light and a detection light in a detection wavelength region different from the observation wavelength region,
    wherein the light source is operatively positioned relative to the elongated insertable structure to emit the observation light and the detection light from the elongated insertable structure;
  an image sensor configured to be controlled to:
    in the observation image acquisition operation, acquire an observation image; and
    in the detection image acquisition operation, acquire a detection image;
  a processor comprising hardware, wherein the processor is configured to implement a determination module configured to determine whether the elongated insertable structure is inserted into the inside of the observed object based on the detection image acquired in the detection image acquisition operation;
  a switch configured to switch between:
    in the observation image acquisition operation, outputting the observation image to a display; and
    in the detection image acquisition operation, outputting the detection image to the determination module of the processor; and
  a controller configured to:
    in the observation image acquisition operation, control the light source to emit the observation light in the observation wavelength region, control the image sensor to acquire the observation image, and control the switch to output observation image to the display; and
    in the detection image acquisition operation, control the light source to emit the one of no light and the detection light in the detection wavelength region different from the observation wavelength region, control the image sensor to acquire the detection image, and control the switch to output the detection image to the determination module of the processor.

21. The observation apparatus according to claim 20,
wherein the observation wavelength region is a wavelength region of visible light, and
wherein in the detection image acquisition operation, the controller is configured to control the light source to emit no light.

22. The observation apparatus according to claim 21,
wherein the image sensor comprises a plurality of pixels,
  wherein each of the plurality of pixels is configured to detect a light quantity of light in the detection wavelength region, and
  wherein the determination module is configured to determine whether the elongated insertable structure is inserted into the inside of the observed object based on one of:
    a maximum light quantity of the plurality of light quantities detected by the plurality of pixels of the image sensor; and
    the plurality of light quantities in a descending order from the maximum light quantity,
    wherein the one of the maximum light quantity and the plurality of light quantities in the descending order is a determination index.

23. The observation apparatus according to claim 22,
wherein the determination module is configured to determine that the elongated insertable structure is not inserted into the inside of the observed object based on a determination that the determination index is equal to or greater than a threshold light quantity, and wherein the determination module is configured to determine that the elongated insertable structure is inserted into the inside of the observed object based on a determination that the determination index is less than the threshold light quantity.

\* \* \* \* \*